(12) United States Patent
Craig

(10) Patent No.: US 8,722,759 B2
(45) Date of Patent: May 13, 2014

(54) FILLERS AND COMPOSITE MATERIALS WITH ZIRCONIA AND SILICA NANOPARTICLES

(75) Inventor: Bradley D. Craig, Lake Elmo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 326 days.

(21) Appl. No.: 13/123,749

(22) PCT Filed: Oct. 9, 2009

(86) PCT No.: PCT/US2009/060104
§ 371 (c)(1),
(2), (4) Date: Apr. 12, 2011

(87) PCT Pub. No.: WO2010/045105
PCT Pub. Date: Apr. 22, 2010

(65) Prior Publication Data
US 2011/0196062 A1     Aug. 11, 2011

Related U.S. Application Data

(60) Provisional application No. 61/105,488, filed on Oct. 15, 2008.

(51) Int. Cl.
*A61L 24/02* (2006.01)
*A61L 24/06* (2006.01)
*A61K 6/08* (2006.01)
*A61K 6/083* (2006.01)
*A61K 6/02* (2006.01)

(52) U.S. Cl.
USPC ........ 523/116; 523/113; 523/115; 433/222.1; 433/224; 433/226; 433/228.1; 977/919

(58) Field of Classification Search
CPC ..... A61K 6/08; A61K 6/0088; A61K 6/0008; A61K 6/024; A61K 6/0073; A61L 24/0089
USPC ............... 523/116, 113, 115; 433/222.1, 224, 433/226, 228.1; 977/919
See application file for complete search history.

(56) References Cited

U.S. PATENT DOCUMENTS

| 2,984,628 A | 5/1961 | Alexander |
| 3,018,262 A | 1/1962 | Schroeder |
| 3,066,112 A | 11/1962 | Bowen |

(Continued)

FOREIGN PATENT DOCUMENTS

| CN | 1188640 | 7/1998 |
| CN | 1212865 | 4/1999 |

(Continued)

OTHER PUBLICATIONS

Adamson, "Aminoalkyl Tertiary Carbinols and Derived Products", *Journal of the Chemical Society*, (1949), Part 1, pp. 144-152.

(Continued)

*Primary Examiner* — Michael Pepitone
(74) *Attorney, Agent, or Firm* — Nicole J. Einerson

(57) ABSTRACT

Fillers containing silica-zirconia nanoclusters are disclosed. The fillers may be prepared by mixing a sol of silica nanoparticles with a sol of preformed, crystalline nanozirconia particles. The fillers provide desirable optical properties, such as opalescence, and are useful in dental compositions.

21 Claims, 1 Drawing Sheet

(56) References Cited

U.S. PATENT DOCUMENTS

| | | | |
|---|---|---|---|
| 3,442,817 A | 5/1969 | Luebke | |
| 3,514,252 A | 5/1970 | Levy | |
| 3,539,533 A | 11/1970 | Lee | |
| 3,629,187 A | 12/1971 | Waller | |
| 3,709,706 A | 1/1973 | Sowman | |
| 3,709,866 A | 1/1973 | Waller | |
| 3,729,313 A | 4/1973 | Smith | |
| 3,741,769 A | 6/1973 | Smith | |
| 3,793,041 A | 2/1974 | Sowman | |
| 3,808,006 A | 4/1974 | Smith | |
| 4,141,144 A | 2/1979 | Lustgarten | |
| 4,158,641 A | 6/1979 | Miyai | |
| 4,250,053 A | 2/1981 | Smith | |
| 4,267,097 A | 5/1981 | Michl | |
| 4,308,190 A | 12/1981 | Walkowiak | |
| 4,389,497 A | 6/1983 | Schmitt | |
| 4,427,799 A | 1/1984 | Orlowski | |
| 4,503,169 A | 3/1985 | Randlev | |
| 4,544,359 A | 10/1985 | Waknine | |
| 4,567,030 A | 1/1986 | Yuasa | |
| 4,612,138 A | 9/1986 | Keiser | |
| 4,617,327 A | 10/1986 | Podszun | |
| 4,649,165 A | 3/1987 | Kuhlmann | |
| 4,652,274 A | 3/1987 | Boettcher | |
| 4,695,251 A | 9/1987 | Randklev | |
| 4,719,091 A | 1/1988 | Wusirika | |
| 4,769,351 A | 9/1988 | Soumiya | |
| 4,772,436 A | 9/1988 | Tyszblat | |
| 4,772,511 A | 9/1988 | Wood | |
| 4,778,671 A | 10/1988 | Wusirika | |
| 4,784,794 A | 11/1988 | Kato | |
| 4,872,936 A | 10/1989 | Engelbrecht | |
| 4,931,414 A | 6/1990 | Wood | |
| 4,946,665 A | 8/1990 | Recasens | |
| 5,037,579 A | 8/1991 | Matchett | |
| 5,234,870 A | 8/1993 | Osaka | |
| 5,275,759 A | 1/1994 | Osaka | |
| 5,350,782 A | 9/1994 | Sasaki | |
| 5,432,130 A | 7/1995 | Rheinberger | |
| 5,470,910 A | 11/1995 | Spanhel | |
| 5,501,727 A | 3/1996 | Wang | |
| 5,593,781 A | 1/1997 | Nass | |
| 5,609,675 A | 3/1997 | Noritake | |
| 5,618,763 A | 4/1997 | Frank | |
| 5,628,806 A * | 5/1997 | Celikkaya et al. | 51/309 |
| 5,643,497 A | 7/1997 | Kaga | |
| 5,698,483 A | 12/1997 | Ong | |
| 5,856,373 A | 1/1999 | Kaisaki | |
| 5,879,715 A | 3/1999 | Higgins | |
| 5,914,185 A | 6/1999 | Shoher | |
| 5,935,275 A | 8/1999 | Burgard | |
| 5,936,006 A | 8/1999 | Rheinberger | |
| 6,020,395 A | 2/2000 | Angeletakis | |
| 6,030,606 A | 2/2000 | Holmes | |
| 6,063,830 A | 5/2000 | Deguchi | |
| 6,121,344 A | 9/2000 | Angeletakis | |
| 6,232,367 B1 | 5/2001 | Kobashigawa | |
| 6,306,926 B1 | 10/2001 | Bretscher | |
| 6,362,251 B1 | 3/2002 | Alkemper | |
| 6,376,590 B2 | 4/2002 | Kolb | |
| 6,387,981 B1 | 5/2002 | Zhang | |
| 6,458,868 B1 | 10/2002 | Okada | |
| 6,565,973 B2 | 5/2003 | Duff | |
| 6,572,693 B1 | 6/2003 | Wu | |
| 6,579,919 B2 | 6/2003 | Konings | |
| 6,627,327 B2 | 9/2003 | Reidt | |
| 6,632,528 B1 | 10/2003 | Clough | |
| 6,648,957 B1 | 11/2003 | Andes | |
| 6,730,156 B1 | 5/2004 | Windisch | |
| 6,747,073 B1 | 6/2004 | Pfaff | |
| 6,899,948 B2 | 5/2005 | Zhang | |
| 6,933,327 B2 | 8/2005 | Yamakawa | |
| 6,984,261 B2 | 1/2006 | Cummings | |
| 7,022,173 B2 | 4/2006 | Cummings | |
| 7,137,818 B2 | 11/2006 | Savic | |
| 7,351,281 B2 | 4/2008 | Hermansson | |
| 7,429,422 B2 | 9/2008 | Davidson | |
| 2002/0189405 A1 | 12/2002 | Liu | |
| 2003/0158289 A1 | 8/2003 | Rusin | |
| 2003/0166740 A1 | 9/2003 | Mitra | |
| 2003/0181541 A1 | 9/2003 | Wu | |
| 2003/0195273 A1 | 10/2003 | Mitra | |
| 2005/0064369 A1 | 3/2005 | Zel | |
| 2005/0175552 A1 | 8/2005 | Hoic | |
| 2005/0252413 A1 | 11/2005 | Kangas | |
| 2005/0252414 A1 | 11/2005 | Craig | |
| 2005/0256223 A1 | 11/2005 | Kolb | |
| 2006/0052232 A1 * | 3/2006 | Bretscher et al. | 501/133 |
| 2007/0248927 A1 | 10/2007 | Luchterhandt | |
| 2008/0200587 A1 * | 8/2008 | Filiatrault et al. | 523/202 |
| 2009/0075239 A1 | 3/2009 | Abuelyaman | |
| 2010/0089286 A1 | 4/2010 | Craig | |

FOREIGN PATENT DOCUMENTS

| | | |
|---|---|---|
| DE | 32 01 109 | 7/1983 |
| DE | 33 16 852 | 11/1984 |
| DE | 103 51 885 | 5/2004 |
| EP | 0 189 540 | 8/1986 |
| EP | 0 201 031 | 11/1986 |
| EP | 0 201 778 | 11/1986 |
| EP | 0 238 025 | 9/1987 |
| EP | 0 373 384 | 6/1990 |
| EP | 0 530 926 | 3/1993 |
| EP | 1 051 961 | 11/2000 |
| EP | 1 329 430 | 7/2003 |
| EP | 1 400 232 | 3/2004 |
| EP | 1 484 046 | 12/2004 |
| JP | 58-079818 | 5/1983 |
| JP | 60-011407 | 1/1985 |
| JP | 60-135468 | 7/1985 |
| JP | 60-137827 | 7/1985 |
| JP | 61-051011 | 3/1986 |
| JP | 61-295259 | 3/1987 |
| JP | 62-065932 | 3/1987 |
| JP | 62-091421 | 4/1987 |
| JP | 62-128924 | 6/1987 |
| JP | 63-176335 | 7/1988 |
| JP | 1115849 | 5/1989 |
| JP | 6-157230 | 6/1994 |
| JP | 6-247825 | 9/1994 |
| JP | 07-041315 | 2/1995 |
| JP | 7196428 | 8/1995 |
| JP | 9-194674 | 7/1997 |
| JP | 2005263648 | 9/2005 |
| WO | WO96/34829 | 11/1996 |
| WO | WO98/13008 | 4/1998 |
| WO | WO99/17716 | 4/1999 |
| WO | WO00/03688 | 1/2000 |
| WO | WO 00/20494 | 4/2000 |
| WO | WO01/30304 | 5/2001 |
| WO | WO01/30305 | 5/2001 |
| WO | WO01/30306 | 5/2001 |
| WO | WO01/30307 | 5/2001 |
| WO | WO01/92271 | 12/2001 |
| WO | WO03/063804 | 8/2003 |
| WO | WO2004/000743 | 12/2003 |
| WO | WO2004/060327 | 7/2004 |
| WO | WO2005/097043 | 10/2005 |
| WO | WO 2005/117805 | 12/2005 |
| WO | WO2007/098878 | 9/2007 |
| WO | WO2008/083275 | 7/2008 |

OTHER PUBLICATIONS

Blumenthal, "The Chemical Behavior of Zirconium," D. Van Nostrand Company, Princeton, NJ, © (1958), pp. 311-338.

Burgard, "Routes to Deagglomerated Nanopowder by Chemical Synthesis," *Materials Research Society*, Mat. Res. Soc. Symp. Proc., vol. 346, (1994), pp. 101-107.

Burgard, "Synthesis and Colloidal Processing of Nanocrystalline (Y2O3-Stabilized) ZrO2 Powders by a Surface Free Energy Controlled Process," *Materials Research Society*, Mat. Res. Soc. Symp., Proc., vol. 432, (1997), pp. 113-121.

(56) References Cited

OTHER PUBLICATIONS

Chatry, "The Role of Complexing Ligants in the Formation of Non-Aggregated Nanoparticles of Zirconia," Chatry, *Journal of Sol-Gel Science and Technology*, vol. 1, (1994), pp. 233-240.

Chen, "Synthesis of Artificial Opals with Uniform Mesoporous Silica Spheres", *Chemistry Letters* (2004), vol. 33, No. 7, pp. 838-839.

Craig, "Direct Esthetic Restorative Materials," *Restorative Dental Materials*, 8th ed., (1989), p. 256-257.

Egon Matijevic, Surface and Colloid Science, vol. 6, ed., Wiley Interscience, Potsdam, NY, (1973), pp. 23-29.

Escobedo, "Preparation of Size Controlled Nanometric Spheres of Colloidal Silica for Synthetic Opal Manufacture", *Materials Science Forum* (2006), vol. 509, pp. 187-192.

Joen, "Hydrothermal Synthesis of ER-Doped Luminescent $TiO_2$ Nanoparticles", *Chem. Mater.*, (2003), vol. 15, No. 6, pp. 1256-126.

Li, "Fabrication of $TiO_2$ Inverse Opal Film and its Application in Chemical Sensor",*ACTA Cihmica Sinica* (2006), vol. 64, No. 14, pp. 1489-1494.

Liz-Marzán, "Three-Dimensional Assemblies of Silica-Coated Metal Nanoparticles", IPAP Conference Series 3 (2001), (*Proceedings of the International Symposium on Cluster Assembled Materials*, 2001), pp. 84-87.

Wan, "Bio-Inspired Polymer Dental Composites with Ordered Filler Arrangement", *ACS Polymeric Materials: Science and Engineering*. Fall Meeting (2006), vol. 95, *Polymeric Materials: Science & Engineering*, pp. 583-584.

Wang, "Fabrication of Two- and Three-Dimensional Silica Nanocolloidal Particle Arrays", *Journal of Physical Chemistry B* (2003), vol. 107, No. 15, pp. 3400-3404.

Zhang, "Monodisperse $SiO_2$ Nanospheres Prepared by Batch/Semibatch Process and Its Opals", *Diffusion and Defect Data—Solid State Data, Pt. B: Solid State Pehnomena* (2007), vol. 121-123, pp. 179-182.

Zhou, "A Novel Tailored Bimodal Porous Silica with Well-Defined Inverse Opal Microstructure and Super-Microporous Lamellar Nanostructure", *Chemical Communications*, Cambridge, UK, (Sep. 11, 2003), vol. 20, pp. 2564-2565.

\* cited by examiner

FILLERS AND COMPOSITE MATERIALS WITH ZIRCONIA AND SILICA NANOPARTICLES

CROSS REFERENCE TO RELATED APPLICATIONS

This application is a national stage filing under 35 U.S.C. 371 of PCT/US2009/060104, filed Oct. 9, 2009, which claims priority to Provisional Application Ser. No. 61/105,488, filed Oct. 15, 2008, the disclosures of which are incorporated by reference in their entirety herein.

TECHNICAL FIELD

The present invention relates to nanoparticle fillers for use in composite materials, including dental composite materials. More specifically, the invention relates to filler materials with silica-zirconia nanoclusters that provide desirable optical properties, such as opalescence, for use in dental compositions.

BACKGROUND

Over the past several decades, there has been an increasing demand among dentists and dental patients for more aesthetic dental restorations. The dental industry's growing focus on aesthetic dentistry has led to the development of dental restorative compositions that more closely mimic the appearance of natural teeth. For example, tooth-colored, composite resin materials have been developed that can be used in place of, for example, metal amalgam fillings, to provide more natural looking dental restorations. In recent years, highly aesthetic composite materials containing silica and/or zirconia nanofillers have become available with shading systems and opacity options that make it possible for a dentist to create dental restorations so natural looking they are virtually undetectable to the casual observer.

Natural tooth enamel has an opalescent quality to it in that it preferentially bends the shorter (blue) wavelengths of light, appearing bluish against a dark background, and more orange/yellow against a white background. Although opalescent dental composites have been developed, this property is often lacking from dental composites that use a silica-zirconia nanofiller system. Despite the many beneficial properties offered by silica-zirconia nanofillers, lack of opalescence may be seen as a drawback. Thus, there remains a need for filler systems, especially silica-zirconia nanofiller systems, that provide dental composites having opalescent properties to better mimic the appearance of natural teeth, while still maintaining suitable handling, radiopacity, clarity, translucence, and other desirable properties of dental composites.

SUMMARY

The present invention features fillers for use in composite materials. The fillers include clusters of zirconia and silica nanoparticles that provide opalescence and radiopacity, along with excellent optical clarity in both reflectance and transmission.

The filler may be prepared by (a) providing a zirconia sol comprising preformed, crystalline zirconia nanoparticles with a diameter from about 3 nm to about 30 nm, (b) providing a silica sol comprising silica nanoparticles with a diameter from about 10 nm to about 100 nm, (c) combining the zirconia sol and the silica sol to form a mixture of zirconia and silica nanoparticles, and (d) heating the mixture to a temperature from about 450° C. to about 950° C. and subsequently milling the resultant material to form a filler comprising silica-zirconia nanoclusters with a diameter from about 0.25 micron to about 50 micron.

Typically, the nanozirconia sol is acid reduced prior to mixing with the nanosilica sol. In some implementations, the silica nanoparticles and zirconia nanoparticles are uniformly distributed in the resulting nanoclusters. Optionally, the method further includes a step of surface treating the silica-zirconia nanoclusters with, for example, a silane coupling agent or similar treatment to assist with incorporation into the resin component.

The zirconia-silica fillers of the invention are useful in composite materials, including dental composite materials. Such composites typically include, a polymerizable component, such as a methacrylate or other ethylenically unsaturated compound, an initiator system, and a filler comprising the silica-zirconia nanoclusters. These composite materials typically have a $C_{ab}$ value of at least 15, more typically at least 18, and most typically at least 20.

Typically, the dental composites of the invention have a refractive index from about 1.44 to about 1.65, more typically from about 1.50 to about 1.6, most typically from about 1.50 to about 1.56. The composites also typically exhibit excellent handling characteristics, radiopacity, low haze (typically less than 70, more typically less than 60, and most typically less than 55 haze units), and possess a directionally independent clarity or translucence, i.e. the clarity is less dependent on the angle of the transmitted light through the material, which make them useful in a variety of dental and orthodontic applications, including as dental restoratives (e.g. filling materials, flowable restoratives, preformed crowns and bridges, temporary restoratives), dental adhesives, dental cements, cavity liners, orthodontic adhesives, dental sealants, dental coatings, and the like. The compositions and related methods may be used to prepare dental articles by hardening to form, for example, dental fillings, dental mill blanks, dental crowns and bridges, dental prostheses, orthodontic devices, and the like.

The above summary is not intended to describe each embodiment or every implementation of the invention. Other embodiments, features, and advantages of the present invention will be apparent from the following detailed description thereof, and from the claims.

DEFINITIONS

By "crystalline zirconia" is meant a zirconia that exhibits significant crystalline (monoclinic, tetragonal, cubic or pseudo-cubic) peaks on X-ray diffraction. Typically, the crytalline zirconia meets the crystallinity parameters of the zirconia sols described in U.S. Pat. No. 6,376,590 (Kolb et al), filed on Oct. 28, 1999, or in U.S. Pat. No. 7,429,422 (Davidson et al), filed on Jun. 7, 2007, both of which are incorporated by reference herein in their entirety.

By "preformed" crystalline zirconia nanoparticles is meant that the sol that is used to fabricate the filler has zirconia particles within it that are crystalline before drying and firing of the filler.

By "sol" is meant a colloid that has a continuous liquid phase in which a solid is suspended in a liquid. Typically, a sol is a stable colloidal suspension of solid particles of 1-500 nm in diameter in a liquid, and particles are usually not agglomerated or aggregated.

As used herein, "hardenable" is descriptive of a material or composition that can be cured (e.g., polymerized or crosslinked) or solidified, for example, by removing solvent (e.g., by evaporation and/or heating); heating to induce polymerization and/or crosslinking; irradiating to induce polymerization and/or crosslinking; and/or by mixing one or more components to induce polymerization and/or crosslinking.

By "dental composition" is meant an unfilled or filled (e.g. a composite) material (e.g., a dental or orthodontic material) that are capable of being applied or adhered to an oral surface. Dental compositions include, for example, adhesives (e.g., dental and/or orthodontic adhesives), cements (e.g., glass ionomer cements, resin-modified glass ionomer cements, and/or orthodontic cements), primers (e.g., orthodontic primers), restoratives (e.g., a restorative filling material), liners, sealants (e.g., orthodontic sealants), and coatings. Oftentimes a dental composition can be used to bond a dental article to a tooth structure.

By "hardenable dental composition" is meant a dental composition, such as a paste, that can be hardened to form a dental article.

By "dental article" is meant an article that can be adhered (e.g., bonded) to an oral surface (e.g., a tooth structure). Typically, the dental article is a restored dentition or a portion thereof. Examples include restoratives, replacements, inlays, onlays, veneers, full and partial crowns, bridges, implants, implant abutments, copings, anterior fillings, posterior fillings, cavity liners, sealants, dentures, posts, bridge frameworks and other bridge sturctures, abutments, orthodontic appliances and devices, and prostheses (e.g., partial or full dentures).

As used herein, the terms "dental composition" and "dental article" are not limited to compositions and articles used in dental applications, but also include orthodontic compositions (e.g., orthodontic adhesives) and orthodontic devices (e.g., orthodontic appliances such as retainers, night guards, brackets, buccal tubes, bands, cleats, buttons, lingual retainers, bite openers, positioners, and the like), respectively.

By "oral surface" is meant a soft or hard surface in the oral environment.

Hard surfaces typically include tooth structure including, for example, natural and artificial tooth surfaces, bone, tooth models, dentin, enamel, cementum, and the like By "filler" is meant a particulate material suitable for use in the oral environment. Dental fillers generally have an average particle size of at most 100 micrometers.

By "nanofiller" is meant a filler having an average primary particle size of at most 200 nanometers. The nanofiller component may be a single nanofiller or a combination of nanofillers. Typically the nanofiller comprises non-pyrogenic nanoparticles or nanoclusters. By "nanostructured" is meant a material in a form having at least one dimension that is, on average, at most 200 nanometers (e.g., nanosized particles). Thus, nanostructured materials refer to materials including, for example, nanoparticles as defined herein below; aggregates of nanoparticles; materials coated on particles, wherein the coatings have an average thickness of at most 200 nanometers; materials coated on aggregates of particles, wherein the coatings have an average thickness of at most 200 nanometers; materials infiltrated in porous structures having an average pore size of at most 200 nanometers; and combinations thereof. Porous structures include, for example, porous particles, porous aggregates of particles, porous coatings, and combinations thereof.

As used herein "nanoparticles" is synonymous with "nanosized particles," and refers to particles having an average size of at most 200 nanometers. As used herein for a spherical particle, "size" refers to the diameter of the particle. As used herein for a non-spherical particle, "size" refers to the longest dimension of the particle. In certain embodiments, the nanoparticles are comprises of discrete, non-aggregated and non-agglomerate particles.

By "nanocluster" is meant an association of nanoparticles drawn together by relatively weak intermolecular forces that cause them to clump together, i.e. to aggregate. Typically, nanoclusters have an average size of at most 10 micrometers.

As used herein, the term "ethylenically unsaturated compound" is meant to include monomers, oligomers, and polymers having at least one ethylenic unsaturation.

By "polymerization" is meant the forming of a higher weight material from monomer or oligomers. The polymerization reaction also can involve a cross-linking reaction.

As used herein, the term "(meth)acrylate" is a shorthand reference to acrylate, methacrylate, or combinations thereof, and "(meth)acrylic" is a shorthand reference to acrylic, methacrylic, or combinations thereof. As used herein, "(meth)acrylate-functional compounds" are compounds that include, among other things, a (meth)acrylate moiety.

The terms "comprises", "comprising" and variations thereof do not have a limiting meaning where these terms appear in the description and claims.

The recitation herein of numerical ranges by endpoints is intended to include all numbers subsumed within that range (e.g. 1 to 5 includes 1, 1.5, 2, 2.75, 3, 3.80, 4, and 5).

As used herein, "a" or "an" means "at least one" or "one or more" unless otherwise indicated. In addition, the singular forms "a", "an", and "the" include plural referents unless the content clearly dictates otherwise. Thus, for example, reference to a composition containing "a compound" includes a mixture of two or more compounds.

As used in this specification and the appended claims, the term "or" is generally employed in its sense including "and/or" unless the content clearly dictates otherwise.

Unless otherwise indicated, all numbers expressing quantities of ingredients, measurement of properties such as contrast ratio and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

BRIEF DESCRIPTION OF THE DRAWINGS

In FIG. 1A, the composite material (2) is viewed straight on by the observer (1). In this situation, Examples E1-E3 and Comparative Examples CE1 and CE2 were clear. In FIG. 1B, the composite material (2) is viewed at an angle relative to the observer (1). In this situation, Examples E1-E3 remained clear, but Comparative Examples CE1 and CE2 were more opaque than when they were viewed straight on.

DETAILED DESCRIPTION

Figure 1A:
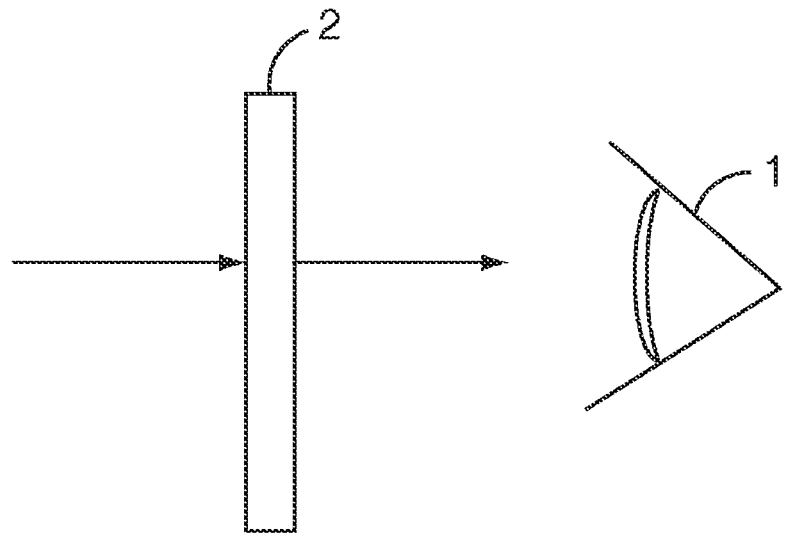
FIGS. 1A and B are diagrams showing the difference between angle-dependent translucent composites and angle-independent translucent composites.

The invention provides filler materials composed of nanoparticles of silica ($SiO_2$) and nanoparticles of zirconia ($ZrO_2$). The silica and zirconia nanoparticles are typically clumped together in the form silica-zirconia nanoclusters. In some implementations of the invention, the nanoparticles of silica and nanoparticles of zirconia are evenly distributed throughout the nanoclusters, which may optionally be surface treated with a silane or other suitable coupling agent to enhance their incorporation into a resin.

The silica-zirconia nanocluster fillers of the invention are prepared by mixing a nanosilica sol together with a preformed nanozirconia particulate sol. The nanozirconia sol is typically composed of crystalline zirconia nanoparticles. It is believed that the source of zirconia affects the opalescence of the resulting filler material. As is demonstrated in the examples below, the use of a preformed nanozirconia sol, in certain circumstances, provides for silica-zirconia nanofillers with better opalescence properties than those derived from zirconyl acetate. In particular, composite materials containing the silica-zirconia nanocluster filler of the invention, typically exhibit an opalescence value ($C_{ab}$) of at least 15, more typically at least 18, and most typically at least 20. Silica-zirconia nanocluster fillers derived from zirconyl acetate typically have a lower opalescence value, or lack opalescence altogether.

In addition to opalescence, the silica-zirconia nanocluster filler materials, in some embodiments, also provide radiopacity, clarity and an optical transparency that is less dependent upon the angle at which the material is viewed when compared to fillers derived from zirconyl acetate. Such optical properties provide materials that are very lifelike in appearance when compared to natural dentition, and are desirable in a variety of product areas, including flowable dental restorative materials, preformed dental crowns and bridges, temporary dental materials, and other restorative dental materials.

The silica-zirconia nanocluster fillers of the invention may be used in a variety of different composite materials, and are particularly suitable for use in hardenable dental compositions. Such materials typically include a polymerizable component, an initiator system, one or more fillers, and one or more optional additives. Each of these components is discussed in more detail below.

Polymerizable Component

The dental compositions of the present invention are typically hardenable due the presence of a polymerizable component. In some embodiments, the compositions can be hardened (e.g., polymerized by conventional photopolymerization and/or chemical polymerization techniques) prior to applying it to an oral surface. In other embodiments, the compositions can be hardened (e.g., polymerized by conventional photopolymerization and/or chemical polymerization techniques) after it has been applied to an oral surface.

In certain embodiments, the compositions are photopolymerizable, i.e., the compositions contain a photoinitiator system that upon irradiation with actinic radiation initiates the polymerization (or hardening) of the composition. In other embodiments, the compositions are chemically hardenable, i.e., the compositions contain a chemical initiator (i.e., initiator system) that can polymerize, cure, or otherwise harden the composition without dependence on irradiation with actinic radiation. Such chemically hardenable compositions are sometimes referred to as "self-cure" compositions.

The polymerizable component typically includes one or more ethylenically unsaturated compounds with or without acid functionality. Examples of useful ethylenically unsaturated compounds include acrylic acid esters, methacrylic acid esters, hydroxy-functional acrylic acid esters, hydroxy-functional methacrylic acid esters, and combinations thereof.

The compositions, especially in photopolymerizable implementations, may include compounds having free radically active functional groups that may include monomers, oligomers, and polymers having one or more ethylenically unsaturated group. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl(meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl(meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate trimethacrylate; (meth)acrylamides (i.e., acrylamides and methacrylamides) such as (meth)acrylamide, methylene bis-(meth)acrylamide, and diacetone(meth)acrylamide; urethane(meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), acrylated oligomers such as those of U.S. Pat. No. 4,642,126 (Zador et al.), and poly(ethylenically unsaturated) carbamoyl isocyanurates such as those disclosed in U.S. Pat. No. 4,648,843 (Mitra); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

The polymerizable component may also contain hydroxyl groups and ethylenically unsaturated groups in a single molecule. Examples of such materials include hydroxyalkyl (meth)acrylates, such as 2-hydroxyethyl(meth)acrylate and 2-hydroxypropyl(meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are also available from a wide variety of commercial sources, such as Sigma-Aldrich, St. Louis. Mixtures of ethylenically unsaturated compounds can be used if desired.

In certain embodiments, the polymerizable component includes PEGDMA (polyethyleneglycol dimethacrylate having a molecular weight of approximately 400), bisGMA, UDMA (urethane dimethacrylate), GDMA (glycerol dimethacrylate), TEGDMA (triethyleneglycol dimethacrylate), bisEMA6 as described in U.S. Pat. No. 6,030,606 (Holmes), and/or NPGDMA (neopentylglycol dimethacrylate). Various combinations of these hardenable components can be used if desired.

When the composition contains an ethylenically unsaturated compound without acid functionality, it is generally present in an amount of at least 5% by weight, more typically at least 10% by weight, and most typically at least 15% by weight ethylenically unsaturated compounds without acid functionality, based on the total weight of the unfilled composition. The compositions of the present invention typically include at most 95% by weight, more typically at most 90% by weight, and most typically at most 80% by weight ethylenically unsaturated compounds without acid functionality, based on the total weight of the unfilled composition.

In some embodiments, the polymerizable component may include one or more ethylenically unsaturated compounds with acid functionality. As used herein, ethylenically unsaturated compounds "with acid functionality" is meant to include monomers, oligomers, and polymers having ethylenic unsaturation and acid and/or acid-precursor functionality. Acid-precursor functionalities include, for example, anhydrides, acid halides, and pyrophosphates. The acid functionality can include carboxylic acid functionality, phosphoric acid functionality, phosphonic acid functionality, sulfonic acid functionality, or combinations thereof.

Ethylenically unsaturated compounds with acid functionality include, for example, α,β-unsaturated acidic compounds such as glycerol phosphate mono(meth)acrylates, glycerol phosphate di(meth)acrylates, hydroxyethyl(meth)acrylate (e.g., HEMA) phosphates, bis((meth)acryloxyethyl) phosphate, ((meth)acryloxypropyl)phosphate, bis((meth)acryloxypropyl) phosphate, bis((meth)acryloxy)propyloxy phosphate, (meth)acryloxyhexyl phosphate, bis((meth)acryloxyhexyl)phosphate, (meth)acryloxyoctyl phosphate, bis((meth)acryloxyoctyl) phosphate, (meth)acryloxydecyl phosphate, bis((meth)acryloxydecyl) phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components in the hardenable component system. Also monomers, oligomers, and polymers of unsaturated carbonic acids such as (meth)acrylic acids, aromatic (meth)acrylated acids (e.g., methacrylated trimellitic acids), and anhydrides thereof can be used. Certain preferred compositions of the present invention include an ethylenically unsaturated compound with acid functionality having at least one P—OH moiety.

Certain of these compounds are obtained, for example, as reaction products between isocyanatoalkyl(meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, polymerizable bisphosphonic acids as disclosed for example, in U.S. Provisional Application No. 60/437,106, filed Dec. 30, 2002; AA:ITA: IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and European Pat. Application Publication Nos. EP 712,622 (Tokuyama Corp.) and EP 1,051,961 (Kuraray Co., Ltd.).

Compositions of the present invention can also include combinations of ethylenically unsaturated compounds with acid functionality as described, for example, in U.S. Patent Application Publication No. 2007/0248927 (Luchterhandt et al.), filed on Aug. 11, 2004. The compositions may also include a mixture of ethylenically unsaturated compounds both with and without acid functionality.

When the composition contains an ethylenically unsaturated compound with acid functionality, it is generally present in an amount of at least 1% by weight, more typically at least 3% by weight, and most typically at least 5% by weight ethylenically unsaturated compounds with acid functionality, based on the total weight of the unfilled composition. The compositions of the present invention typically include at most 80% by weight, more typically at most 70% by weight, and most typically at most 60% by weight ethylenically unsaturated compounds with acid functionality, based on the total weight of the unfilled composition.

Initiator System

In certain embodiments, the compositions of the present invention are photopolymerizable, i.e., the compositions contain a photopolymerizable component and a photoinitiator system that upon irradiation with actinic radiation initiates the polymerization (or hardening) of the composition. Such photopolymerizable compositions can be free radically polymerizable or cationically polymerizable.

Suitable photoinitiators (i.e., photoinitiator systems that include one or more compounds) for polymerizing free radically photopolymerizable compositions include binary and tertiary systems. Typical tertiary photoinitiators include an iodonium salt, a photosensitizer, and an electron donor compound as described in U.S. Pat. No. 5,545,676 (Palazzotto et al.). Suitable iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Suitable photosensitizers are monoketones and diketones that absorb some light within a range of 400 nm to 520 nm (preferably, 450 nm to 500 nm). Particularly suitable compounds include alpha diketones that have light absorption within a range of 400 nm to 520 nm (even more preferably, 450 to 500 nm). Suitable compounds are camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Suitable electron donor compounds include substituted amines, e.g., ethyl dimethylaminobenzoate. Other suitable tertiary photoinitiator systems useful for photopolymerizing cationically polymerizable resins are described, for example, in U.S. Pat. No. 6,765,036 (Dede et al.).

Other useful photoinitiators for polymerizing free radically photopolymerizable compositions include the class of phosphine oxides that typically have a functional wavelength range of 380 nm to 1200 nm. Preferred phosphine oxide free radical initiators with a functional wavelength range of 380 nm to 450 nm are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), U.S. Pat. No. 6,251,963 (Kohler et al.); and EP Application No. 0 173 567 A2 (Ying).

Commercially available phosphine oxide photoinitiators capable of free-radical initiation when irradiated at wavelength ranges of greater than 380 nm to 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl)phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Typically, the phosphine oxide initiator is present in the photopolymerizable composition in catalytically effective amounts, such as from 0.1 weight percent to 5.0 weight percent, based on the total weight of the unfilled composition.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from 0.1 weight percent to 5.0 weight percent, based on the total weight of the unfilled composition. Useful amounts of other initiators are well known to those of skill in the art.

In certain embodiments, the compositions of the present invention are chemically hardenable, i.e., the compositions contain a chemically hardenable component and a chemical initiator (i.e., initiator system) that can polymerize, cure, or otherwise harden the composition without dependence on irradiation with actinic radiation. Such chemically hardenable compositions are sometimes referred to as "self-cure" compositions.

The chemically hardenable compositions may include redox cure systems that include a polymerizable component (e.g., an ethylenically unsaturated polymerizable component) and redox agents that include an oxidizing agent and a reducing agent. Suitable polymerizable components, redox agents, optional acid-functional components, and optional fillers that are useful in the present invention are described in U.S. Pat. Publication Nos. 2003/0166740 (Mitra et al.) and 2003/0195273 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. Pat. Publication No. 2003/0195273 (Mitra et al.).

The reducing and oxidizing agents are present in amounts sufficient to permit an adequate free-radical reaction rate. This can be evaluated by combining all of the ingredients of the composition except for the optional filler, and observing whether or not a hardened mass is obtained.

Typically, the reducing agent, if used at all, is present in an amount of at least 0.01% by weight, and more typically at least 0.1% by weight, based on the total weight (including water) of the components of the composition. Typically, the reducing agent is present in an amount of no greater than 10% by weight, and more typically no greater than 5% by weight, based on the total weight (including water) of the components of the unfilled composition.

Typically, the oxidizing agent, if used at all, is present in an amount of at least 0.01% by weight, and more typically at least 0.10% by weight, based on the total weight (including water) of the components of the composition. Typically, the oxidizing agent is present in an amount of no greater than 10% by weight, and more typically no greater than 5% by weight, based on the total weight (including water) of the components of the unfilled composition.

The reducing or oxidizing agents can be microencapsulated as described in U.S. Pat. No. 5,154,762 (Mitra et al.). This will generally enhance shelf stability of the composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

A redox cure system can be combined with other cure systems, including photoinitiator systems or with a composition such as described U.S. Pat. No. 5,154,762 (Mitra et al.).

Silica-Zirconia Nanoclusters

The composition of the invention includes a silica-zirconia nanocluster filler that imparts the composition with opalescence. It is believed that the opalescent effect stems, at least in part, from the utilization of preformed nanozirconia particles when forming the silica-zirconia cluster. Use of these preformed particles provides a filler with superior opalescence over that obtained when starting from other precursors such as, for example, an acetate salt.

The nanoclusters can be prepared by combining a sol of silica nanoparticles with a sol of preformed, crystalline zirconia nanoparticles. The silica sol typically comprises silica particles having a mean diameter from about 10 nm to about 100 nm, more typically from about 15 nm to about 60 nm, most typically from about 15 nm to about 35 nm, with a mean particle diameter of about 20 nm being particularly well-suited for fabrication of nanoclusters. The zirconia sol typically comprises zirconia particles that are small enough to not scatter the majority of visible light, but are large enough to bend shorter wavelength blue light to give the opalescent effect. A zirconia sol having a mean particle size from about 3 nm to about 30 nm is suitable for forming the nanoclusters. Typically, the zirconia particles in the sol have a mean particle diameter from about 5 nm to about 15 nm, more typically from about 6 nm to about 12 nm, and most typically from about 7 nm to about 10 nm. When mixed together under acidic conditions where the sol mixture is stable, such as at a pH of below 2, the preformed zirconia nanoparticles form a structure with the silica nanoparticles on gelling and drying that gives the desired opalescence character while maintaining a high level of optical transparency of the final composite material.

NALCO 1042 silica sol (Nalco Chemical Company, Naperville, Ill.) or other commercially available colloidal silica sols may be used. If a base-stabilized sol is used, typically it will first be subjected to ion exchange in order to remove sodium, for example, with an Amberlite IR-120 ion exchange resin, or pH adjusted with Nitric acid. It is usually desirable to pH adjust the silica to below 1.2, typically about 0.8 to about 1.0, and then add the zirconia to it slowly, to prevent localized gelation and agglomeration. The pH of the resultant mixture is typically about 1.1 to about 1.2. Suitable colloidal silica sols are available from a variety of vendors, including Nalco (Ondeo-Nalco, Grace chemical), H. C. Stark, Nissan Chemical (Snowtex), Nyacol, and Ludox (DuPont). The selected sol should have silica particles that are discrete and of the appropriate size specified herein. The silica sol may be treated to provide a highly acidic silica sol (e.g., nitrate stabilized) that can be mixed with the zirconia sol without gelation.

The zirconia sol may be obtained using the process described in U.S. Pat. No. 6,376,590 (Kolb, et al.), filed on Oct. 28, 1999, or U.S. Pat. No. 7,429,422 (Davidson et al.), filed Jun. 7, 2007. As used herein, the term "zirconia" refers to various stoichiometries for zirconium oxides, most typically $ZrO_2$, and may also be known as zirconium oxide or zirconium dioxide. The zirconia may contain up to 30 weight percent of other chemical moieties such as, for example, $Y_2O_3$ and organic material.

The silica-zirconia nanoclusters can be prepared by mixing together the nanosilica sol with the nanozirconia sol, and heating the mixture to at least 450° C. Typically, the mixture is heated for 4 to 24 hours at a temperature between about 400 to about 1000° C., more typically from about 450 to about 950° C., to remove water, organic materials, and other volatile components, as well as to potentially weakly aggregate the particles (not required). Alternatively, or in addition, the sol mixture may undergo a different processing step to remove water and volatiles. The resulting material may be milled or ground and classified to remove large aggregates. The filler may then be surface treated with, for example, a silane prior to mixing with a resin.

The amount of filler used in the composite material will depend on the particular application, as described in more detail below. Typically, for dental restorative compositions, the filler content is between about 40 weight percent and 90 weight percent of the composition. It some implementations, it is also desirable for the refractive index (RI) of the filler to substantially match that of the resin (i.e., the RI of the filler only differs from the RI of the resin by an amount from about 0.02 to about 0.05 RI units).

As used herein, "index of refraction," or "refractive index," refers to the absolute refractive index of a material (e.g., a monomer) that is understood to be the ratio of the speed of electromagnetic radiation in free space to the speed of the radiation in that material. The refractive index can be measured using known methods and, for example, using an Abbe refractometer in the visible light region (available commercially, for example, from Fisher Instruments of Pittsburgh, Pa.). It is generally appreciated that the measured index of refraction can vary to some extent depending on the instrument. Measurements are typically run in accordance with the instrument manufacturer's recommendations and good laboratory practices. The refractive index values of may also be measured by dispersing a test sample (typically at room temperature) into optical liquids with different known specific refractive indexes. A kit with calibrated optical liquids is available from Cargille Laboratories (Cedar Grove, N.J.) for this purpose. Observations of the dispersions are with a light microscope. The refractive index of the solid material may be determined using the Becke's line as a band of light that appears along the outer edge of the dispersed particles under microscopic investigation. The Becke's line indicates the relative difference or the equality between the refractive indices of the solid material and the optical liquid.

Additional Filler(s)

In addition to the silica-zirconia nanocluster filler, the compositions of the present invention may optionally contain one or more other fillers. These fillers may be selected from one or more of a wide variety of materials suitable for incorporation in compositions used for dental applications, such as fillers currently used in dental restorative compositions, and the like.

The choice of filler affects important properties of the dental composite such as its appearance, radiopacity and physical and mechanical properties. Appearance is affected in part by adjustment of the amounts and relative refractive indices of the ingredients of the composite, thereby allowing alteration of the translucence, opacity or pearlescence of the composite. In this way, the appearance of the dental material can, if desired, be made to closely approximate the appearance of natural dentition.

Radiopacity is a measurement of the ability of the dental composite to be detected by x-ray examination. Frequently a radiopaque dental composite will be desirable, for instance, to enable the dentist to determine whether or not a dental restoration remains sound. Under other circumstances a non-radiopaque composite may be desirable. Suitable fillers for radiopaque formulations are described in EP-A2-0 189 540, EP-B-0 238 025, and U.S. Pat. No. 6,306,926 B1.

The amount of filler that is incorporated into the composite, referred to herein as the "loading level" and expressed as a weight percent based on the total weight of the dental material, will vary depending on the type of filler, the curable resin and other components of the composition, and the end use of the composite.

For some dental materials, such as sealants, the compositions of the invention can be lightly filled (e.g., having a loading level of less than about 40 weight percent) or unfilled. In such implementations, the viscosity of the dental material is sufficiently low to allow its penetration into pits and fissures of occlusal tooth surfaces as well as into etched areas of enamel, thereby aiding in the retention of the dental material. In applications where high strength or durability are desired (e.g., anterior or posterior restoratives, prostheses, crown and bridge cements, artificial crowns, artificial teeth and dentures) the loading level can be as high as about 95 weight percent. For most dental restorative and prosthetic applications a loading level is generally at least 40 weight percent, and more typically is between about 60 and 90 weight percent.

The filler(s) used in the compositions of the invention is typically finely divided. The filler(s) can have a unimodal or polymodal (e.g., bimodal) particle size distribution. The maximum particle size (the largest dimension of a particle, generally, the diameter or by volumetric average) of the filler(s) is typically less than 50 micrometers, more typically less than 10 micrometers, and most typically less than 5 micrometers. In some embodiments, number average particle size of the filler(s) is typically less than 0.5 micrometers, and more typically less than 0.2 micrometer, but in other embodiments the average particle size may be larger, and the material may include particles with a maximum particle size around 40 micrometers.

The filler(s) may be an inorganic material. It may also be a crosslinked organic material that is insoluble in the resin system, and is optionally filled with inorganic filler. The filler(s) should in any event be nontoxic and suitable for use in the mouth. The filler(s) can be radiopaque or radiolucent. The filler typically is substantially insoluble in water.

In addition to the $SiO_2$—$ZrO_2$ nanoclusters, examples of other suitable inorganic fillers that may be included in the composition are naturally occurring or synthetic materials including, but not limited to: quartz (i.e. silica, $SiO_2$); nitrides (e.g., silicon nitride); glasses derived from, for example, Zr, Sr, Ce, Sb, Sn, Ba, Zn, and Al; feldspar; borosilicate glass; kaolin; talc; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Degussa Corp., Akron, Ohio and CAB-O-SIL M5 silica from Cabot Corp., Tuscola, Ill.). In some embodiments, the silica or nanosilica particles are non-pyrogenic, i.e. comprise non-fumed silica. Examples of suitable organic filler particles include filled or unfilled pulverized olycarbonates, polyepoxides, and the like. The additional filler(s) may be acid-reactive, non-acid-reactive, or a combination thereof.

Metallic fillers may also be incorporated, such as particulate metal filler made from a pure metal such as those of Groups IVA, VA, VIA, VIIA, VIII, IB, or IIB, aluminum, indium, and thallium of Group IIIB, and tin and lead of Group IVB, or alloys thereof Conventional dental amalgam alloy powders, typically mixtures of silver, tin, copper, and zinc, may also optionally be incorporated. The particulate metallic filler preferably has an average particle size of about 1 micron to about 100 microns, more preferably 1 micron to about 50 microns. Mixtures of these fillers are also contemplated, as well as combination fillers made from organic and inorganic materials. Fluoroaluminosilicate glass fillers, either untreated or silanol treated, are particularly preferred. These glass fillers have the added benefit of releasing fluoride at the site of dental work when placed in the oral environment.

In some implementations, the composition may include acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses are particularly preferred. The FAS glass, if present, typically contains sufficient elutable cations so that a hardened dental composition will form when the glass is mixed with the components of the hardenable composition. The glass also typically contains sufficient elutable fluoride ions so that the hardened composition will have cariostatic properties. Such glass can be made from a melt containing fluoride, alumina, and other glass-forming ingredients using techniques familiar to those skilled in the FAS glassmaking art. The FAS glass, if present, is typically in the form of particles that are sufficiently finely divided so that they can conveniently be mixed with the other cement components and will perform well when the resulting mixture is used in the mouth.

Generally, the average particle size (typically, diameter) for FAS glass used in such compositions is no greater than about 12 micrometers, typically no greater than 10 micrometers, and more typically no greater than 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEM-FIL Superior (Dentsply International, York, Pa.). Mixtures of fillers can be used if desired.

The surface of the filler particles can also be treated with a coupling agent in order to enhance the bond between the filler and the resin. Suitable coupling agents include gamma-methacryloxypropyltrimethoxysilane, gamma-mercaptopropyltriethoxysilane, gamma-aminopropyltrimethoxysilane, and the like. Silane-treated zirconia-silica ($ZrO_2$—$SiO_2$) fillers and nanofillers, silane-treated silica fillers and nanofillers, silane-treated zirconia fillers and nanofillers, and combinations thereof are especially suitable for certain restorative compositions. Other suitable fillers are disclosed in U.S. Pat. No. 6,387,981 (Zhang et al.); U.S. Pat. No. 6,572,693 (Wu et al.); U.S. Pat. No. 6,730,156 (Windisch); and U.S. Pat. No. 6,899,948 (Zhang); as well as in International Publication No. WO 03/063804 (Wu et al.). Filler components described in these references include nanosized silica particles, nanosized metal oxide particles, and combinations thereof. Nanofillers are also described in U.S. Patent Publication Nos. 2005/0252413 (Kangas et al.); 2005/0252414 (Craig et al.); and 2005/0256223 (Kolb et al.).

For some embodiments of the present invention that include filler (e.g., dental adhesive compositions), the compositions typically include at least 1% by weight, more typically at least 2% by weight, and most typically at least 5% by weight filler, based on the total weight of the composition. For such embodiments, compositions of the present invention typically include at most 40% by weight, more typically at most 20% by weight, and most typically at most 15% by weight filler, based on the total weight of the composition.

For other embodiments (e.g., wherein the composition is a dental restorative or an orthodontic adhesive), compositions of the present invention typically include at least 40% by weight, more typically at least 45% by weight, and most typically at least 50% by weight filler, based on the total weight of the composition. For such embodiments, compositions of the present invention typically include at most 90% by weight, more typically at most 80% by weight, even more typically at most 70% by weight filler, and most typically at most 50% by weight filler, based on the total weight of the composition.

Other Additives

Optionally, compositions of the present invention may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), or mixtures thereof.

In some implementations of the invention, the compositions are non-aqueous. In other implementation, the compositions may optionally contain water. The water can be distilled, deionized, or plain tap water. If present, the amount of water should be sufficient to provide adequate handling and mixing properties and/or to permit the transport of ions, particularly in a filler-acid reaction. In such embodiments, water represents at least about 1 wt-%, and more preferably at least about 5 wt-%, of the total weight of ingredients used to form the hardenable composition. Generally, water represents no greater than about 75 wt-%, and more preferably no greater than about 50 wt-%, of the total weight of ingredients used to form the hardenable composition.

If desired, the compositions of the invention may contain additives such as indicators, dyes (including photobleachable dyes), pigments, inhibitors, accelerators, viscosity modifiers, wetting agents, antioxidants, tartaric acid, chelating agents, buffering agents, stabilizers, diluents, and other similar ingredients that will be apparent to those skilled in the art. Surfactants, for example, nonionic surfactants, cationic surfactants, anionic surfactants, and combinations thereof, may optionally be used in the compositions. Useful surfactants include non-polymerizable and polymerizable surfactants. Additionally, medicaments or other therapeutic substances can be optionally added to the dental compositions. Examples include, but are not limited to, fluoride sources, whitening agents, anticaries agents (e.g., xylitol), remineralizing agents (e.g., calcium phosphate compounds and other calcium sources and phosphate sources), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions. Combination of any of the above additives may also be employed. The selection and amount of any one such additive can be selected by one of skill in the art to accomplish the desired result without undue experimentation.

Preparation and Use of Dental Compositions Containing Silica-Zirconia Filler

The dental compositions of the present invention can be prepared by combining all the various components using conventional mixing techniques. The resulting composition may optionally contain fillers, solvents, water, and other additives as described herein. Typically, photopolymerizable compositions of the invention are prepared by simply admixing, under "safe light" conditions, the components of the inventive compositions. Suitable inert solvents may be employed if desired when affecting this mixture. Any solvent may be used which does not react appreciably with the components of the inventive compositions. Examples of suitable solvents include acetone, dichloromethane, acetonitrile and lactones. A liquid material to be polymerized may be used as a solvent for another liquid or solid material to be polymerized. Solventless compositions can be prepared by simply dissolving the (optional) iodonium complex salt, sensitizer, and electron donor in the polymerizable resin, with or without the use of mild heating to facilitate dissolution.

The amounts and types of each ingredient in the dental material should be adjusted to provide the desired physical and handling properties before and after polymerization. For example, the polymerization rate, polymerization stability, fluidity, compressive strength, tensile strength and durability of the dental material typically are adjusted in part by altering the types and amounts of polymerization initiator(s) and the loading and particle size distribution of filler(s). Such adjustments typically are carried out empirically based on previous experience with dental materials. When the dental material is applied to a tooth, the tooth can optionally be pre-treated with a primer and/or an adhesive by methods known to those skilled in the art.

The compositions can be supplied in a variety of forms including one-part systems and multi-part systems, e.g., two-part powder/liquid, paste/liquid, paste/powder and paste/paste systems. Other forms employing multi-part combinations (i.e., combinations of two or more parts), each of which is in the form of a powder, liquid, gel, or paste are also possible. The various components of the composition may be divided up into separate parts in whatever manner is desired; however, in a redox multi-part system, one part typically contains the oxidizing agent and another part typically contains the reducing agent, though it is possible to combine the reducing agent and oxidizing agent in the same part of the system if the components are kept separated, for example, through use of microencapsulation. Also, for those implementation in which the dental composition is a resin-modified glass ionomer (RMGI), the polyacid, acid-reactive filler and water generally would not all be present in the same part, although any two of these may be grouped together in the same part along with any combination of other components.

The components of the composition can be included in a kit, where the contents of the composition are packaged to allow for storage of the components until they are needed.

The components of the composition can be mixed and clinically applied using conventional techniques. A curing light is generally required for the initiation of photopolymerizable compositions. The compositions may be in the form of composites or restoratives that adhere very well to dentin and/or enamel. Optionally, a primer layer can be used on the tooth tissue on which the hardenable composition is used.

The invention encompasses a wide variety of dental compositions. Exemplary dental materials include dental restoratives (e.g., composites, fillings, sealants, inlays, onlays, crowns, and bridges), orthodontic appliances, and orthodontic adhesives. Such dental materials include direct aesthetic restorative materials (e.g., anterior and posterior restoratives), prostheses, adhesives and primers for oral hard tissues, sealants, veneers, cavity liners, orthodontic bracket adhesives for use with any type of bracket (such as metal, plastic and ceramic), crown and bridge cements, artificial crowns, artificial teeth, dentures, and the like. These dental materials are used in the mouth and are disposed adjacent to natural teeth. The phrase "disposed adjacent to" as used herein refers to the placing of a dental material in temporary or permanent bonding (e.g., adhesive) or touching (e.g., occlusal or proximal) contact with a natural tooth.

The features and advantages of the invention are further illustrated by the following examples, which are in no way intended to be limiting thereof. The particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

EXAMPLES

Unless otherwise noted, reagents and solvents were obtained from Sigma-Aldrich Corp., St. Louis, Mo.

As used herein,

"bisGMA" refers to 2,2-bis[4-(2-hydroxy-3-methacryloyloxypropoxy)phenyl]propane;

"TEGDMA" refers to triethyleneglycol dimethacrylate, obtained from Sartomer Co., Inc., Exton, Pa.;

"UDMA" refers to diurethane dimethacrylate, obtained under the trade designation "ROHAMERE 6661-0" from Rohm America LLC, Piscataway, N.J.;

"BisEMA6" refers to ethoxylated bisphenol A dimethacrylate, obtained from Sartomer Co., Inc., Exton, Pa.;

"BHT" refers to butylated hydroxytoluene;

"BZT" refers to 2-(2-Hydroxy-5-Methacryloxyethylphenyl)-2H-Benzotriazole obtained from Ciba, Inc., Tarrytown, N.Y.;

"ENMAP" refers to ethyl-(N-methyl-N-phenyl)amino propionate, synthesized using known methods, such as those described by Adamson, et al.; JCSOA9; J. Chem. Soc.; 1949; spl. 144,152, which is incorporated herein by reference;

"CPQ" refers to camphorquinone;

"Irgacure 819" refers to a Bis(2,4,6-Trimethylbenzoyl) phenylphosphine oxide obtained from Ciba, Inc., Tarrytown, N.Y.;

"PEG 600 DM" refers to Polyethylene Glycol Dimethacrylate, avg MW ~600, available from Sartomer Co., Inc., Exton, Pa.; and "GENIOSIL GF-31" or "GF-31" refers to a 3-methacryloxypropyltrimethoxysilane composition available from Wacker Chemie AG, Munich, Germany.

Preparation of Resin A

A resin was made by mixing together the components in the relative amounts shown in table 1 below (all amounts are weight fractions):

TABLE 1

Resin A Formulation.

| Component | Amount (weight fraction) |
| --- | --- |
| TEGDMA | 0.011900 |
| BisGMA | 0.247298 |
| UDMA | 0.346201 |
| BisEMA6 | 0.346201 |
| PEG 600 DM | 0.037601 |
| CPQ | 0.001551 |
| Igracure 819 | 0.002501 |
| ENMAP | 0.004001 |
| BHT | 0.001499 |
| BZT | 0.001247 |

Preparation of Filler A:

Filler A was prepared by weighing 105.24 g NALCO 1042 silica sol, adding 3.15 g 70 wt % $HNO_3$ solution, and adding this to 45.16 g of acid reduced zirconia sol (prepared essentially as described in U.S. Pat. No. 7,429,422 (Davidson et al,), filed Jun. 7, 2007). This resulted in an oxide mixture of approximately 73 wt % silica to 27 wt % zirconia on an oxide weight basis. To this mixture was added 100 g of granulated sugar. The resulting sol was poured into a ceramic vessel and fired at 625 C to remove volatile and organic materials. The resulting fired material was subsequently ground with a mortar and pestle and screened through a 75 micron nylon mesh to remove large agglomerates. The material was then silane treated by mixing together 25.000 g of the resultant ground oxide, 3.270 g GF-31 silane, 27.4 g ethyl acetate, and 0.447 g 30% $NH_4OH$ solution. This was allowed to mix for approximately 4 hours before flashing off the ethyl acetate in a pyrex tray, and then heating at 90 C for 30 minutes.

Preparation of Filler B (No Sugar):

Filler B was prepared by weighing 45.16 g acid reduced zirconia sol (prepared essentially as described in U.S. Pat. No. 7,429,422, (Davidson, et al.), filed Jun. 7, 2007), and to this was added a mixture of 105.65 g NALCO 1042 silica sol and 1.19 g 70 wt % nitric acid solution. This mixture was poured directly into a ceramic firing vessel, and fired at 625 C for 4 hours to remove water and organic volatiles. This resultant oxide was also approximately 73 wt % silica to 27 wt % zirconia. The resulting filler was ground with a mortar and pestle, screened through a 75 micron nylon mesh to remove large agglomerates. 40 g of this material was added to 6.02 g GF-31 silane, 49 g ethyl acetate, and 0.76 g 30% NH4OH solution. It was reacted for 3 hours, the solvent flashed off in a pyrex tray, and the material baked at 90 C for 30 min for the final filler.

Preparation of Filler C:

Filler C was prepared with the same ratios of materials as described above for Filler B. The filler was heated to 825 C for 8 hours (instead of 625 C) and milled in a ball mill instead of a mortar and pestle and the filler was silane treated by dispersing in 1-methoxy-2-propanol, and heated to 80 C for 3 hours at a pH of 8.75 (NH4OH adjusted) with an 11% GF-31 charge to the weight of the filler and the materials was then gap dried.

Preparation of Filler D (Negative Control):

A silane treated silica/zirconia filler derived from zirconyl acetate with a ratio of approximately 73% silica to 27% zirconia was prepared essentially as described in Preparatory Examples A and B of U.S. Pat. No. 6,730,156, except that the filler was calcined again after milling at 713° C. for 11 hours before silanting to remove additional residuals.

Examples E1-E3 and Comparative Examples CE1-CE2

Several different pastes were made by mixing components together as set forth in table 2 below.

TABLE 2

Paste Formulations.

| | |
| --- | --- |
| Example 1 (E1) | 70 wt % Filler A with 30 wt % Resin A |
| Example 2 (E2) | 70 wt % Filler B with 30 wt % Resin A |
| Example 3 (E3) | 70 wt % Filler C with 30 wt % Resin A |
| Comparative Example 1 (CE1) | 70 wt % Filler D with 30 wt % Resin A |
| Comparative Example 3 (CE2) | FILTEK SUPREME PLUS™ translucent shade material (unpigmented), available from 3M Company, St. Paul, MN (silica only filler). |

Pastes E1, E2, E3, and CE2 showed significant opalescence to the naked eye, appearing orange/yellow on a white background, and blue/white on a black background. Pastes CE1 did not show opalescent character to the naked eye, appearing yellow on both a black and white background, to the naked eye. All pastes appeared translucent to transparent.

Opalescence was measured quantitatively for pastes E1, E3, CE1, and CE2 on a HunterLab Ultrascan XE (Hunter Associates Laboratory, Inc., Reston Va., USA) spectrophotometer with the value $C_{ab}$ (opalescence) measured by taking the difference as described below between the a* and b* values measured in reflectance against a black background, and in transmittance mode. This is the difference in the vector in the a-b plane of color space for the two measurements. Results are shown in Table 3.

Samples were prepared by making in a metal ring an optical disc of the composites (~1.3 g each) of 1 inch in diameter, and 1 mm thickness (+/−0.02 mm) of the composite discs by pressing discs in a mold curing under mylar film with an XL 3000 dental curing light over the entire surface of the disc in 9 overlapping points for 20 seconds each to insure full cure. These discs were taken to the hunter unit, and after calibration for large sample usage (1 inch) and the larger aperature opening, measurements were taken in reflectance mode against a black background. The instrument was recalibrated for transmission measurements, and then readings were taken in transmission mode, and haze measurements were also taken in the transmission mode. L*, a*, b* coordinates (for both reflectance and transmission) and haze values (for transmission only) were recorded. $C_{ab}$ was calculated by: $C_{ab}=((b^*_{ref}-b^*_{trans})^2+(a^*_{ref}-a^*_{trans})^2)^{1/2}$

TABLE 3

Opalescence Measurements.

| Paste | $C_{ab}$ |
|---|---|
| E1 | 24.114 |
| E3 | 21.068 |
| CE1 | 7.0378 |
| CE2 | 20.420 |

As can be seen in table 3, the samples containing Filler A and Filler C, with the silica-zirconia nanoclusters formed from a pre-formed zirconia particle, gave more opalescence than the paste containing silica/zirconia filler derived from zirconyl acetate (CE1). The opalescence is also in a range that is very similar to FILTEK SUPREME PLUS™ (CE2) translucent shade (silica only), which is very desirable and near that of natural enamel.

Haze measurements for E3 and CE1 were taken directly from the transmission measurement on the instrument, and are provided in Table 4. The sample containing the opalescent Filler C exhibited significantly lower haze than the sample containing silica/zirconia filler derived from zirconyl acetate (CE1).

TABLE 4

Haze Measurements.

| Paste | Haze |
|---|---|
| E3 | 47.34 |
| CE1 | 86.23 |

Figure 1B:
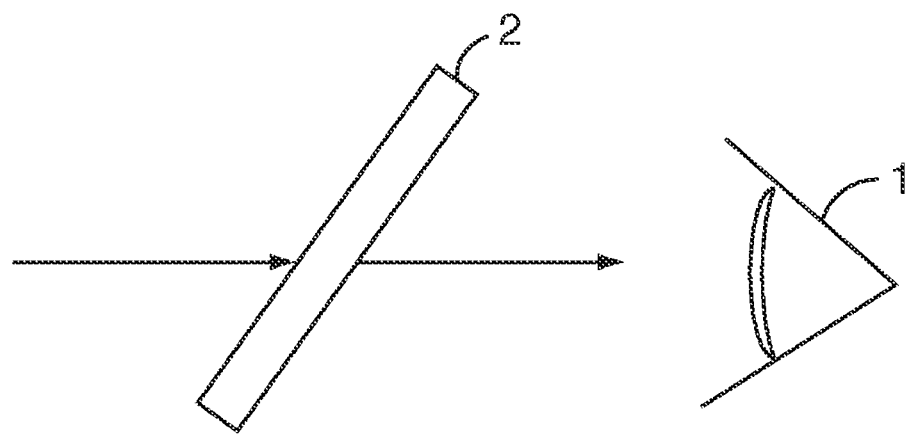

Pastes made with this opalescent silica-zirconia filler (E1, E2, and E3) also had the interesting optical effect of having less angular dependence on the transmission of light. This effect, illustrated in FIG. 1, has the potential to give a more vibrant, lifelike restoration when used in a dental restorative. The new materials also are able to transmit images more clearly through them when removed further from the object viewed behind them than conventional pastes.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

The complete disclosures of the patents, patent documents, and publications cited herein are incorporated by reference in their entirety as if each were individually incorporated.

What is claimed is:

1. A method of making a filler for a composite material, the method comprising:
   (a) providing a zirconia sol comprising preformed, crystalline zirconia nanoparticles with a mean diameter from about 3 nm to about 30 nm,
   (b) providing a silica sol comprising silica nanoparticles with a mean diameter from about 10 nm to about 100 nm,
   (c) combining the zirconia sol and the silica sol to form a mixture of zirconia and silica nanoparticles,
   (d) heating the mixture to a temperature from about 400° C. to about 1000° C. and
   (e) milling the heated mixture to form a filler comprising silica-zirconia nanoclusters.

2. The method of claim 1, wherein the nanoclusters have a mean volumetric diameter from about 0.01 to about 100 micrometers.

3. The method of claim 1, wherein the nanoclusters have a mean volumetric diameter from about 0.5 to about 10 micrometers.

4. The method of claim 1, wherein the silica nanoparticles have a mean diameter from about 15 nm to about 35 nm and the zirconia nanoparticles have a mean diameter from about 5 nm to about 15 nm.

5. The method of claim 1, wherein the silica nanoparticles and zirconia nanoparticles are uniformly distributed in the nanoclusters.

6. The method of claim 1, further comprising lowering the pH of the silica sol to below 1.2 prior to mixing with the zirconia sol.

7. The method of claim 1, wherein the silica-zirconia filler has a refractive index from about 1.44 to about 1.65.

8. The method of claim 1, wherein the zirconia sol is acid reduced.

9. A hardenable dental composition comprising:
   (a) a polymerizable component,
   (b) an initiator system, and
   (c) a filler comprising nanoclusters of zirconia nanoparticles and silica nanoparticles,
   wherein the composition has a $C_{ab}$ value of at least 15 when measured according to the Opalescence Test Method.

10. The composition of claim 9, wherein the silica nanoparticles have a mean diameter from about 15 nm to about 60 nm.

11. The composition of claim 9, wherein the zirconia nanoparticles have a mean diameter from about 5 nm to about 15 nm.

12. The composition claim 9, wherein the silica nanoparticles and zirconia nanoparticles are uniformly distributed in the nanoclusters.

13. The composition of claim 9, wherein composition has a $C_{ab}$ value of at least 18 when measured according to the Opalescence Test Method.

14. The composition of claim 9, wherein the composition has a haze measurement of less than 70 haze units.

15. The composition of claim 9, wherein the nanoclusters are surface treated.

16. The composition of claim 9, wherein the polymerizable component comprises an ethylenically unsaturated compound.

17. The composition of claim 16, wherein the polymerizable component comprises a (meth)acrylate.

18. The composition of claim 9, wherein the composition has a refractive index from about 1.44 to about 1.65.

19. A dental restorative material comprising the dental composite of claim 9.

20. The dental restorative material of claim 19, wherein the material is a filling material, preformed bridge or crown, a flowable restorative, or temporary restorative material.

21. The method of claim 1, wherein heating the mixture occurs at a Temperature from about 450° C. to about 950°C.

* * * * *

UNITED STATES PATENT AND TRADEMARK OFFICE
CERTIFICATE OF CORRECTION

PATENT NO. : 8,722,759 B2
APPLICATION NO. : 13/123749
DATED : May 13, 2014
INVENTOR(S) : Bradley Craig It is certified that error appears in the above-identified patent and that said Letters Patent is hereby corrected as shown below:

Title Page

Page 3, Column 1 (Other Publications)
Line 16, Delete "Cihmica" and insert -- Chimica --, therefor.

Page 3, Column 2 (Other Publications)
Line 14, Delete "Pehnomena" and insert -- Phenomena --, therefor.

In the Specification

Column 2
Line 50, Delete "crytalline" and insert -- crystalline --, therefor.

Column 3
Line 26, Delete "sturctures," and insert -- structures, --, therefor.
Line 41, Delete "like" and insert -- like. --, therefor.

Column 5
Line 47, Delete "initiatior" and insert -- initiator --, therefor.

Column 13
Line 20, Delete "unimodial" and insert -- unimodal --, therefor.
Line 60, Delete "thereof" and insert -- thereof. --, therefor.

Column 18
Line 27, Delete "NH4OH" and insert -- $NH_4OH$ --, therefor.
Line 37, Delete "(NH4OH" and insert -- ($NH_4OH$ --, therefor.
Line 62, Delete "PLUSTM™" and insert -- PLUS™ --, therefor.

Signed and Sealed this
Tenth Day of February, 2015

Michelle K. Lee
*Deputy Director of the United States Patent and Trademark Office*

Column 19
Line 22, Delete "aperature" and insert -- aperture --, therefor.

In the Claims

Column 21
Line 21, In Claim 21, delete "Temperature" and insert -- temperature --, therefor.